US006428552B1

(12) United States Patent
Sparks

(10) Patent No.: US 6,428,552 B1
(45) Date of Patent: Aug. 6, 2002

(54) METHOD AND APPARATUS FOR CROSSING INTRAVASCULAR OCCLUSIONS

(75) Inventor: Kurt D. Sparks, Palo Alto, CA (US)

(73) Assignee: LuMend, Inc., Redwood City, CA (US)

( * ) Notice: Subject to any disclaimer, the term of this patent is extended or adjusted under 35 U.S.C. 154(b) by 0 days.

(21) Appl. No.: 09/768,376

(22) Filed: Jan. 22, 2001

(51) Int. Cl.$^7$ ............................................. A61B 17/22
(52) U.S. Cl. ...................... 606/159; 604/22; 604/96.01
(58) Field of Search ............................ 606/1, 159, 170, 606/171, 180, 192, 194, 195, 198; 604/22, 96.01

(56) References Cited

U.S. PATENT DOCUMENTS

| | | | |
|---|---|---|---|
| 2,687,131 A | 8/1954 | Raiche | 128/349 |
| 3,880,168 A | 4/1975 | Berman | 128/351 |
| 4,538,622 A | 9/1985 | Samson et al. | 128/772 |
| 4,619,274 A | * 10/1986 | Morrison | 128/772 |
| 4,648,402 A | 3/1987 | Santos | 128/345 |
| 4,748,986 A | 6/1988 | Morrison et al. | 128/772 |
| 4,838,268 A | 6/1989 | Keith et al. | 128/344 |
| 4,906,241 A | * 3/1990 | Noddin et al. | 606/194 |
| 4,934,380 A | 6/1990 | de Toledo | 128/772 |
| 4,998,917 A | 3/1991 | Gaiser et al. | 604/96 |
| 5,001,556 A | 3/1991 | Nakamura et al. | 358/98 |
| 5,019,040 A | 5/1991 | Itaoka et al. | 604/95 |
| 5,047,040 A | * 9/1991 | Simpson et al. | 606/159 |
| 5,099,850 A | 3/1992 | Matsui et al. | 128/662.06 |
| 5,114,414 A | 5/1992 | Buchbinder | 604/95 |
| 5,127,917 A | 7/1992 | Niederhauser et al. | 606/191 |
| 5,176,661 A | 1/1993 | Evard et al. | 604/282 |
| 5,279,565 A | 1/1994 | Klein et al. | 604/105 |
| 5,290,230 A | * 3/1994 | Ainsworth et al. | 604/96 |
| 5,300,025 A | * 4/1994 | Wantink | 604/96 |
| 5,321,501 A | 6/1994 | Swanson et al. | 356/345 |
| 5,334,169 A | 8/1994 | Brown et al. | 604/282 |
| 5,341,818 A | 8/1994 | Abrams et al. | 128/772 |
| 5,364,357 A | 11/1994 | Aase | 604/96 |
| 5,385,152 A | 1/1995 | Abele et al. | 128/772 |
| 5,409,453 A | 4/1995 | Lundquist et al. | 604/22 |

(List continued on next page.)

FOREIGN PATENT DOCUMENTS

| | | | |
|---|---|---|---|
| DE | 2945237 A1 | * | 5/1981 |
| DE | 4429117 A1 | * | 2/1996 |
| EP | 0377269 | | 7/1990 |
| EP | 0396074 | * | 11/1990 |
| FR | 1585065 | * | 1/1970 |
| WO | WO83/03188 | * | 9/1983 |
| WO | WO91/19528 | | 12/1991 |
| WO | WO92/08510 | | 5/1992 |
| WO | WO93/18818 | | 9/1993 |
| WO | WO95/19143 | | 7/1995 |
| WO | WO96/01590 | | 1/1996 |

*Primary Examiner*—Rodney M. Lindsey
(74) *Attorney, Agent, or Firm*—Perkins Coie LLP

(57) ABSTRACT

An apparatus for treating occlusions. In one embodiment, the apparatus comprises an outer catheter shaft with at least one axial lumen therethrough, wherein the outer catheter shaft comprises a distal end having an outer diameter, and an inner catheter shaft having an average diameter slidably disposed in the at least one axial lumen of the outer catheter shaft. The inner catheter shaft comprises at least one axial lumen therethrough, and an a traumatic, tapered protuberance comprising a distal end and a proximal end, wherein a diameter of the a traumatic, tapered protuberance tapers upward from the average diameter at the distal end to a greatest diameter at the proximal end. The embodiment further comprises a guidewire slidably disposed in the at least one axial lumen of the inner catheter shaft, wherein the guidewire is advanced through the body lumen into the occlusion. When the outer catheter shaft is advanced distally to closely approach the proximal end of the atraumatic, tapered protuberance, the outer catheter shaft and the inner catheter shaft present a relatively smooth tapering surface to the occlusion such that the outer catheter shaft may enter the occlusion.

12 Claims, 5 Drawing Sheets

U.S. PATENT DOCUMENTS

| | | | |
|---|---|---|---|
| 5,449,343 A | * 9/1995 | Samson et al. | 604/96 |
| 5,451,207 A | * 9/1995 | Ainsworth et al. | 604/96 |
| 5,454,788 A | 10/1995 | Walker et al. | 604/96 |
| 5,460,187 A | * 10/1995 | Daigle et al. | 123/772 |
| 5,465,733 A | 11/1995 | Hinohara et al. | 128/772 |
| 5,507,301 A | * 4/1996 | Wasicek et al. | 128/772 |
| 5,520,189 A | 5/1996 | Malinowski et al. | 128/662.03 |
| 5,522,825 A | 6/1996 | Kropf et al. | 606/159 |
| 5,533,987 A | * 7/1996 | Pray et al. | 604/280 |
| 5,573,531 A | 11/1996 | Gregory | 606/14 |
| 5,632,760 A | 5/1997 | Sheiban et al. | 606/191 |
| 5,673,707 A | 10/1997 | Chandrasekaran | 128/772 |
| 5,676,659 A | * 10/1997 | McGurk | 604/282 |
| 5,819,733 A | 10/1998 | Bertram | 128/207 |
| 5,827,324 A | 10/1998 | Cassell et al. | 606/200 |

* cited by examiner

METHOD AND APPARATUS FOR CROSSING INTRAVASCULAR OCCLUSIONS

FIELD OF THE INVENTION

The invention is in the field of intravascular devices. In particular, the present invention is in the field of intravascular devices used to treat near total and total occlusions in tortuous body lumens.

BACKGROUND OF THE INVENTION

The majority of intervention procedures such as balloon angioplasty, atherectomy, stenting and the like bring some degree of relief to the patient and improvement in the blood flow. Total or near total occlusions are difficult to treat, however, as intervention tools such as angioplasty balloons are often too large or blunt to cross the occlusion site. This is generally referred to as an inability to cross, and is one of the major causes of failures of occlusion treatment procedures.

Conventional apparatus are typically ineffective in treating total or near total occlusions. One reason for this is that a conventional guidewire may successfully cross the occlusion, but the catheter that is intended to treat the occlusion cannot enter or cross the occlusion because the catheter is of a substantially greater diameter than the guidewire. This situation is illustrated in FIG. 1. Body lumen 110 is shown in cross-section with an occlusion 120 almost totally blocking the flow of fluid through the occlusion. The occlusion 120 may be of various textures and hardnesses, for example soft and fatty or hard and calcified. The occlusion 120 also may be found at a great variety of sites in the body, such as the arterial system including the aorta, the coronary and carotid arteries, and peripheral arteries. As shown in FIG. 1, a balloon catheter 170 includes a catheter shaft 150 and an inflatable balloon 160. The catheter shaft 150 includes an axial lumen 140, indicated by dashed lines. A guidewire 130 is slidably disposed within the lumen 140. Even when the occlusion 120 is particularly hard and calcified or fibrous in nature, the guidewire 130 may succeed in crossing the occlusion 120. However, the catheter with its working element, such as the inflatable balloon 160, may be unsuccessful in following in the path of the small diameter guidewire 130. The entire assembly must then be retracted in the proximal direction and the catheter removed from the patient's body. Thereafter, other more invasive and traumatic surgical treatment procedures may be necessary to restore a healthy blood flow.

Another reason that conventional apparatus are typically ineffective in treating total or near total occlusions is that conventional catheter shafts and guidewires do not perform well under compressive loading and torque loading. In small and tortuous body lumens, it is often necessary for a physician to push and twist the apparatus in order to navigate the lumen. In typical conventional apparatus the compressive force and torque are not effectively transferred along the length of the apparatus to assist in navigation.

SUMMARY OF THE DISCLOSURE

An apparatus for treating occlusions in body lumens is disclosed. In one embodiment, the apparatus includes an outer catheter shaft, an inner catheter shaft slidably disposed in a lumen of the outer catheter shaft, and a guidewire slidably disposed in a lumen of the inner catheter shaft. The distal end of the outer catheter shaft is significantly larger in diameter than the guidewire and the inner catheter shaft. The inner catheter shaft includes an atraumatic, tapered protuberance that increases in diameter from a distal end of the protuberance to a proximal end of the protuberance. The proximal end of the protuberance is approximately the diameter of the distal end of the outer catheter shaft. The guidewire is advanced through the body lumen up to and into the occlusion. The inner catheter shaft is then advanced over the guidewire until the atraumatic, tapered protuberance contacts the occlusion. The outer catheter shaft is then advanced over the inner catheter shaft so that the distal end of the outer catheter shaft closely approaches the proximal end of the atraumatic, tapered protuberance. When the distal end of the outer catheter shaft closely approaches the proximal end of the atraumatic, tapered protuberance, the outer catheter shaft and the inner catheter shaft present a relatively smooth tapering surface to the occlusion such that the outer catheter shaft may enter the occlusion.

DETAILED DESCRIPTION

A method and apparatus for crossing intravascular occlusions is described. In one embodiment, the apparatus includes an outer catheter shaft and an inner catheter shaft slidably disposed in a lumen in the outer catheter shaft. A guidewire is slidably disposed in a lumen in the inner catheter shaft. In one embodiment, the guidewire is initially pushed through an occlusion. The inner catheter shaft is then advanced over the guidewire to enter the occlusion. The outer catheter shaft is advanced over the inner catheter shaft. The distal end of the outer catheter shaft has a large diameter relative to the diameters of the guidewire and inner catheter shaft. The relatively large diameter is required to open the occlusion. The inner catheter shaft includes an atraumatic, tapered protuberance. When the outer catheter shaft is advanced so that the distal end of the outer catheter shaft closely approaches the proximal end of the atraumatic, tapered protuberance, the occlusion is presented with a smooth, atraumatic transition from the inner catheter shaft to the outer catheter shaft, and the outer catheter shaft is enabled to enter the occlusion. The outer catheter shaft can include some working element, such as an inflatable balloon or a cutting or abrading element which may be deployed when the outer catheter shaft enters the occlusion.

Figure 1:
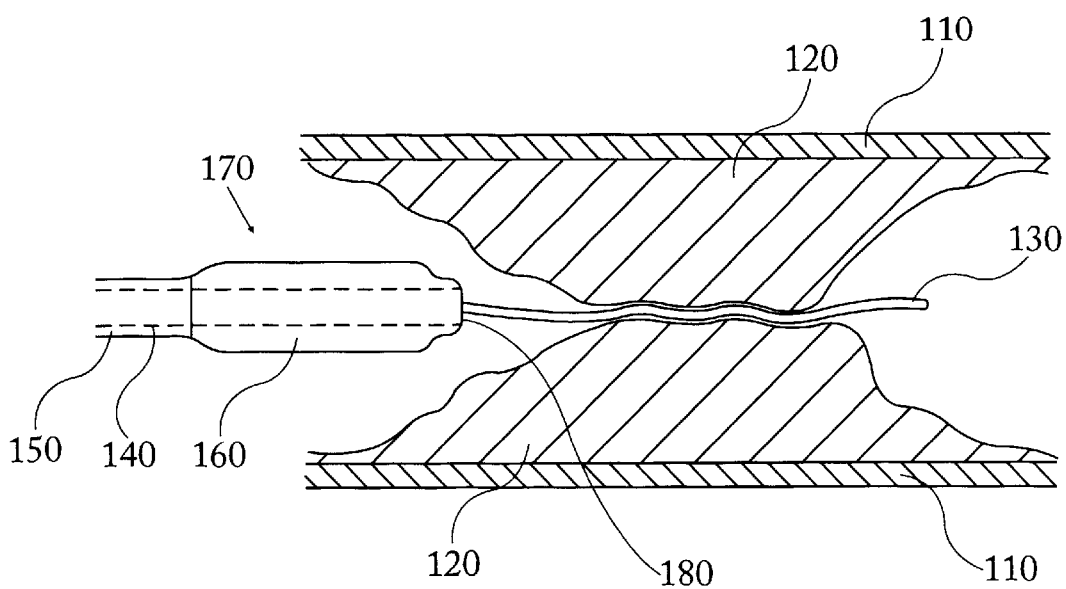
FIG. 1 is a diagram of a prior art catheter, illustrating the difficulty of crossing intravascular occlusions with conventional catheters.
Figure 2:
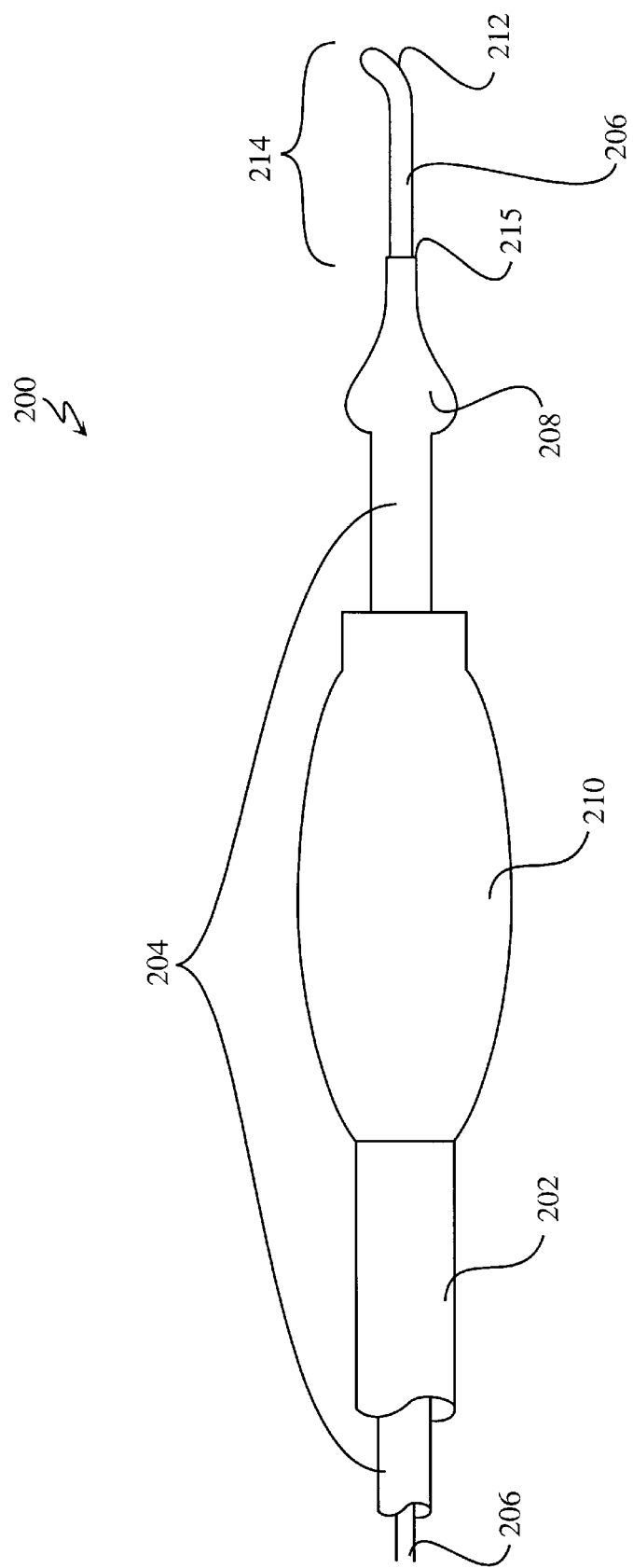
FIG. 2 is a diagram of an embodiment of an apparatus including an atraumatic occlusion widening protuberance on a guidewire.

FIG. 2 is a diagram of another embodiment of an occlusion crossing apparatus 200. The apparatus 200 includes an outer catheter shaft 202, an inner catheter shaft 204, and a guidewire 206. The inner catheter shaft 204 is slidably disposed in a lumen of the outer catheter shaft 202. The guidewire 206 is slidably disposed in a lumen of the inner catheter shaft 204. The inner catheter shaft 204 includes an atraumatic, tapered protuberance 208 having a generally teardrop shape. The inner catheter shaft 204 terminates in the distal end 215. In one embodiment, the guidewire 206 includes a bend 212 in its distal section 214 that assists in directing the guidewire 206 through a body lumen. In other embodiments, the distal section 214 can have any other shape, for example the distal section 214 can be straight or have multiple bends. The outer catheter shaft 202 includes an inflatable balloon 210, which is a working element on the outer catheter shaft 202. Other working elements may be used instead of or in conjunction with the inflatable balloon 210, such as cutting or abrading working elements.

In operation, the guidewire 206 is advanced through a body lumen to and into an occlusion. The inner catheter shaft 204 is advanced over the guidewire 206, and the outer catheter shaft 202 is advanced over the inner catheter shaft 204. In some operational situations, it may be easier to advance the guidewire through a tortuous lumen to the occlusion before advancing the inner catheter shaft 204 with the atraumatic, tapered protuberance 208 through the lumen. The guidewire 206 may advanced as far as necessary through the lumen, including into the occlusion, before the inner catheter shaft 204 or the outer catheter shaft 202 are advanced distally. Once the guidewire 206 is advanced into the occlusion, the inner catheter shaft 204 may be advanced until the atraumatic, tapered protuberance 208 meets or begins to enter the occlusion. Thereafter, the outer catheter shaft 202 may be advanced relative to the inner catheter shaft 204.

Figure 3A:
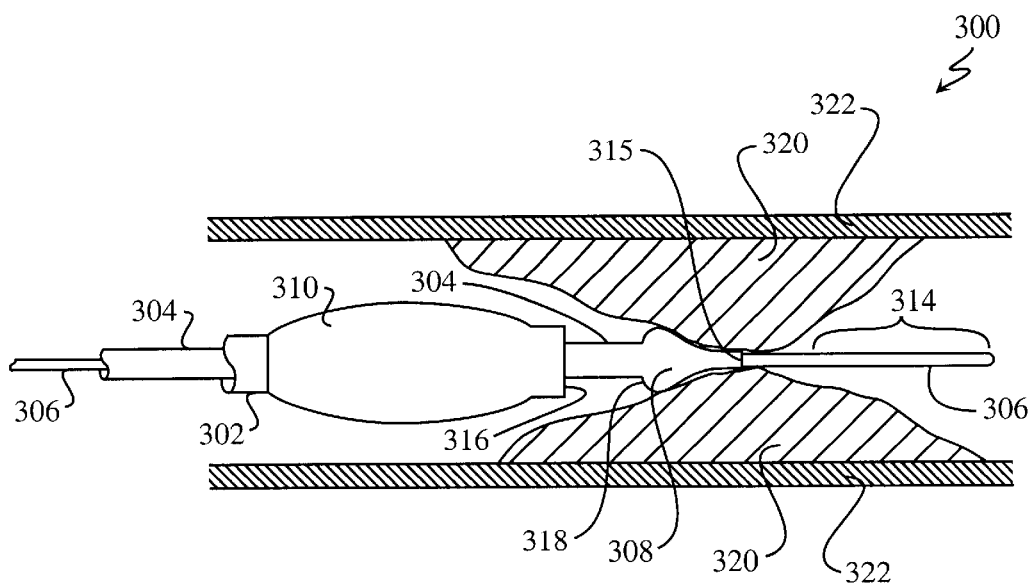
FIG. 3A illustrates an embodiment of a method and apparatus for crossing an occlusion with an atraumatic occlusion widening protuberance on a guidewire.

FIG. 3A is a diagram of one embodiment of a catheter apparatus 300 shown in operation as it enters an occlusion 320 in a body lumen 322. The catheter apparatus 300 includes an outer catheter shaft 302, an inner catheter shaft 304, and a guidewire 306. The catheter apparatus 300 is similar to the catheter apparatus 200 except the distal section 314 of the guidewire 306 is straight rather than bent.

The guidewire distal section 314 has a relatively small average diameter, for example about 0.014 inches, for easily penetrating the occlusion 320. The inner catheter shaft 304 terminates in a distal end 315. The inner catheter shaft 304 has an atraumatic, tapered protuberance 308 that tapers from up from the distal end 315 to a proximal surface 318 of the protuberance 308. The atraumatic, tapered protuberance 308 is tapered toward the distal end 315 such that it provides a smooth transition to the guidewire 306. The guidewire 306 is slidably disposed within the inner catheter shaft 304. In one embodiment, the guidewire 306 is made of a single section of a stock material such as stainless steel or nickel-titanium. The length of the distal section 314 may be as great as required to cross the occlusion, for example in the range of five to thirty centimeters. The length of the atraumatic, tapered protuberance 308 may be varied. In one embodiment, the length of the atraumatic, tapered protuberance 308 is approximately 0.01 to 0.50 inches, depending upon the occlusion to be treated and the flexibility required of the guidewire 306. The atraumatic, tapered protuberance 308 may have a greatest diameter of about 0.016 to 0.022 inches, depending upon the occlusion to be crossed. The atraumatic, tapered protuberance 308 may have any shape that is generally tapered upward from the average diameter of the guidewire 306 and is conducive to atraumatic advancement through the occlusion 320.

The outer catheter shaft 302 has a distal surface 316 perpendicular to the axis of the outer catheter shaft 302. The diameter of the outer catheter shaft 302 adjacent the distal surface 316 is equal to or slightly larger than the greatest diameter of the atraumatic, tapered protuberance 308. Typically, the diameter of the outer catheter shaft 302 adjacent the distal surface 316 is approximately equal to the greatest diameter of the atraumatic, tapered protuberance 308.

Figure 3B:
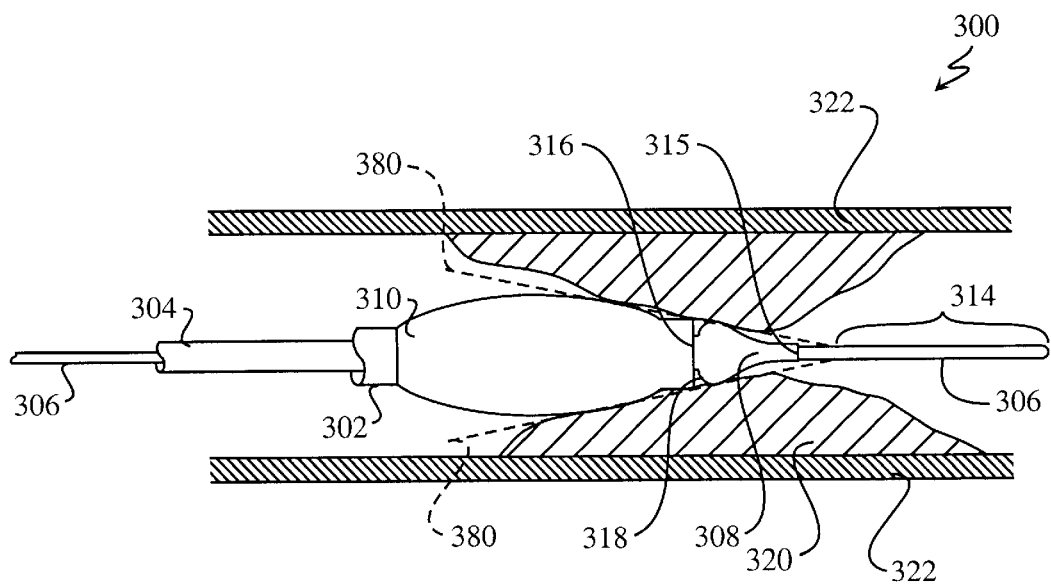
FIG. 3B further illustrates the method and apparatus of FIG. 3A.

FIG. 3B further illustrates the catheter apparatus crossing the total occlusion 320 in the body lumen 322. Once the atraumatic, tapered protrusion 308 reaches the occlusion 320, the operating physician advances the outer catheter shaft 302 distally until the distal surface 316 closely approaches or even contacts the proximal surface 318. When the distal surface 316 of the outer catheter shaft 302 closely approaches the proximal surface 318 of the atraumatic, tapered protuberance 308, the outer catheter shaft 302 and the protuberance 308 form a relatively smooth tapering surface, as outlined by dashed lines 380, which is presented to the occlusion. A smooth, atraumatic transition from the atraumatic, tapered protuberance 308 to the outer catheter shaft 302 is created to enable the outer catheter shaft 302 to enter the occlusion. A biasing force in the proximal direction can be applied to the inner catheter shaft to maintain the distal surface 316 in proximity to the proximal surface 318.

In one embodiment, the outer catheter shaft 302 includes an inflatable balloon 310, which is a working element on the outer catheter shaft 302. The inflatable balloon may be inflated by known methods after entry into the occlusion 320. Inflation methods include introduction of a fluid through fluid lines in a lumen (not shown) of the outer catheter shaft 302. Other embodiments may include other working elements such as cutting or abrading elements.

Figure 4:
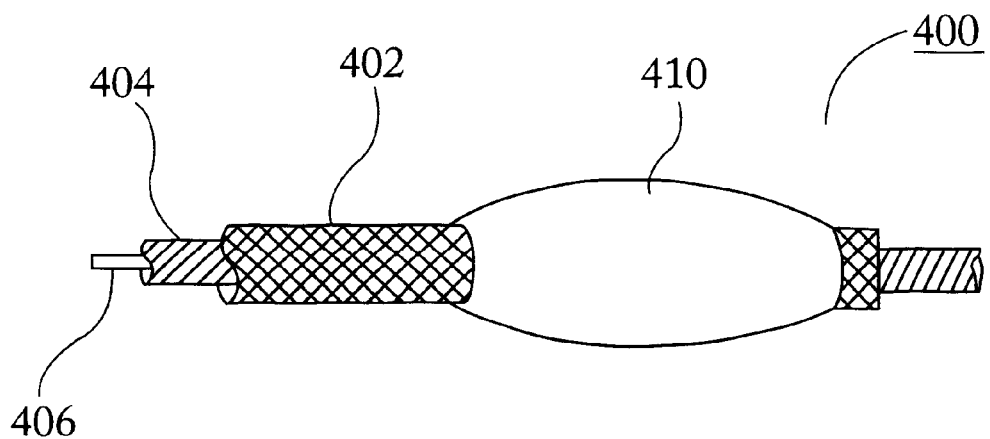
FIG. 4 is a diagram of an inner catheter shaft and an outer catheter shaft with enhanced torque transmission characteristics.

FIG. 4 is a diagram of an embodiment that provides enhanced torque transmission characteristics and enhanced compressive loading characteristics. In negotiating tortuous lumens, an apparatus subjected to compressive force or torque may bunch locally rather than transmitting the force as desired to direct the apparatus. The apparatus 400 includes an outer catheter shaft 402, an inner catheter shaft 404, and a guidewire 406. The apparatus 400 also includes an inflatable balloon 410. The outer catheter shaft 402 may be fabricated using materials that include, in various embodiments, a wire, a coil, or a wire mesh wound about the outer catheter shaft 402. Alternatively, the wire, the coil, or the mesh may be embedded within and/or bonded to the outer catheter shaft 402. The inner catheter shaft 404 may also be fabricated using materials that include a wire, coil, or mesh embedded within, bonded to, and/or wound about its outer diameter. The thickness of the wire, coil, or wire mesh may be selected within a range of 0.001 to about 0.005 inches. Either or both of the outer catheter shaft 402 and the inner catheter shaft 404 may be fabricated using materials that include an extrudable plastic material, such as Tecoflex, polyethylene, PEBAX, polyurethane, nylon and polyamide or a blend or blends of these. By selecting the material, the wire, coil or braid configuration, and the diameter and number of such wires, excellent compressive characteristics and torque characteristics may be achieved for both the outer catheter shaft 402 and the inner catheter shaft 404.

Figure 5:
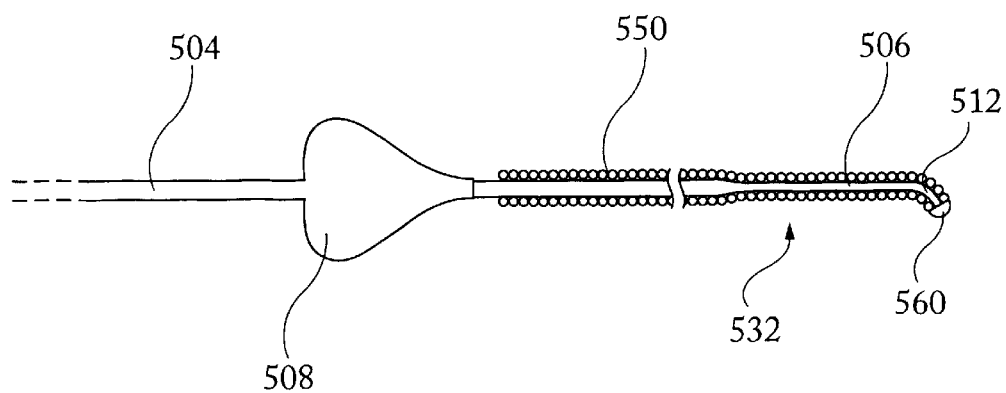
FIG. 5 is a diagram of a guidewire with enhanced torque transmission characteristics.

FIG. 5 is a diagram of an inner catheter shaft 504 and a guidewire 506 of one embodiment. The inner catheter shaft 504 includes an atraumatic, tapered protuberance 508. The guidewire 506 is slidably disposed in a lumen of the inner catheter shaft 504. The guidewire 506 includes a spirally wound wire or plastic coil 550 about its distal section, which is shown in cross-section. The coil 550 may be a single filament or multiple filament coil. The coil 550 may be soldered, welded or glued at its proximal and distal ends, or at intermediate points. The guidewire 506 has a taper 532 that transitions to a smaller diameter toward the distal end of the guidewire 506. The guidewire 506 may include multiple tapers 532. The guidewire 506 also has a bend 512 that allows a physician, by twisting or torqueing the guidewire 506, to navigate turns in a body lumen with the apparatus. The guidewire 506 also has an atraumatic distal cap 560. The atraumatic distal cap 560 covers the distal tip of the guidewire 506. The distal cap 560 is a solder ball in one embodiment.

The present invention has been described with reference to specific embodiments shown in the drawings. Modifications may be made by one of ordinary skill in the art without departing from the spirit and scope of the invention, which is defined by the following claims.

What is claimed is:

1. An apparatus for crossing occlusions in a body lumen, comprising:
    an outer catheter shaft with at least one axial lumen therethrough, wherein the outer catheter shaft comprises a distal end having an outer diameter;
    an inner catheter shaft having an average diameter slidably disposed in the at least one axial lumen of the outer catheter shaft, wherein the inner catheter shaft comprises,
        at least one axial lumen therethrough; and
        an atraumatic, tapered protuberance comprising a distal end and a proximal end, wherein a diameter of the atraumatic, tapered protuberance tapers upward from the average diameter at the distal end to a greatest diameter at the proximal end;
    a guidewire slidably disposed in the at least one axial lumen of the inner catheter shaft, wherein the guidewire is advanced through the body lumen into the occlusion; and
    wherein the outer catheter shaft can be advanced distally to closely approach the proximal end of the atraumatic, tapered protuberance such that the outer catheter shaft and the inner catheter shaft present a relatively smooth tapering surface to the occlusion such that the outer catheter shaft may enter the occlusion.

2. The apparatus of claim 1, wherein the guidewire comprises at least one bend in a distal section of the guidewire to assist in directing the guidewire.

3. The apparatus of claim 1, wherein the outer catheter shaft comprises a working element selected from a group comprising an inflatable balloon, a cutting element, and an abrading element.

4. The apparatus of claim 1, wherein the outer catheter shaft is fabricated using at least one element selected from a group comprising a wire, a coil, a wire braid, and a mesh, and wherein the outer catheter shaft is fabricated using at least one method selected from a group comprising embedding the at least one element in the outer catheter shaft, bonding the at least one element to the outer catheter shaft, and winding the at least one element around the outer catheter shaft.

5. The apparatus of claim 1, wherein the outer catheter shaft is fabricated using at least one element selected from a group comprising Tecoflex, polyethylene, PEBAX, polyurethane, nylon and polyamide.

6. The apparatus of claim 1, wherein the inner catheter shaft is fabricated using at least one element selected from a group comprising a wire, a coil, a wire braid, and a mesh, and wherein the inner catheter shaft is fabricated using at least one method selected from a group comprising embedding the at least one element in the inner catheter shaft, bonding the at least one element to the inner catheter shaft, and winding the at least one element around the inner catheter shaft.

7. The apparatus of claim 1, wherein the inner catheter shaft is fabricated using at least one element selected from a group comprising Tecoflex, polyethylene, PEBAX, polyurethane, nylon and polyamide.

8. The apparatus of claim 1, wherein the guidewire comprises:
    a spirally wound coil about a distal section of the guidewire;
    at least one taper; and
    an atraumatic distal cap at a distal end of the guidewire.

9. A method of treating an occlusion in a body lumen comprising:
    advancing a guidewire of an apparatus into the body lumen and into the occlusion;
    advancing an inner catheter shaft distally over the guidewire until an atraumatic, tapered protrusion of the inner catheter shaft contacts the occlusion;
    advancing an outer catheter shaft distally over the inner catheter shaft until a distal end of the outer catheter shaft closely approaches a proximal end of the atraumatic, tapered protrusion such that the outer catheter shaft and the guidewire present a relatively smooth tapering surface to the occlusion;
    applying a proximal biasing force to the inner catheter shaft so as to maintain the distal end of the outer catheter shaft in close proximity to the proximal end of the atraumatic, tapered protrusion; and
    simultaneously advancing the inner catheter shaft and the outer catheter shaft through the occlusion.

10. The method of claim 9, wherein the guidewire comprises a bend in a distal section of the guidewire, the method further comprising applying torque to the guidewire to direct the guidewire through the body lumen and through the occlusion.

11. The method of claim 9, wherein the outer catheter shaft comprises a working element, and wherein the method further comprises deploying the work element.

12. The method of claim 11, wherein the working element is an inflatable balloon, and wherein deploying comprises inflating the inflatable balloon in the occlusion.

* * * * *